United States Patent [19]
Glover et al.

[11] Patent Number: 5,601,784
[45] Date of Patent: *Feb. 11, 1997

[54] ON-LINE CONTROL AND MONITORING SYSTEM FOR WET LIME/LIMESTONE FLUE GAS DESULFURIZATION PROCESS

[75] Inventors: Robert L. Glover, Southlake, Tex.;
Robert E. Moser, Palo Alto, Calif.;
Frank Meserole, Austin; Carl Richardson, Round Rock, both of Tex.;
Gerard B. Maybach, Getzville, N.Y.;
Gordon Maller, Louisville, Ky.;
Timothy Hanley, Holly Springs, N.C.

[73] Assignee: Electric Power Research Institute, Palo Alto, Calif.

[*] Notice: The term of this patent shall not extend beyond the expiration date of Pat. No. 5,505,854.

[21] Appl. No.: 302,438

[22] Filed: Sep. 9, 1994

[51] Int. Cl.$^6$ .......... G01N 30/02; G01N 21/00; C01B 17/22
[52] U.S. Cl. .......... 422/70; 422/82; 422/82.01; 422/82.03; 422/108; 422/111; 436/43; 436/51; 436/55; 210/96.2; 210/143; 210/739; 423/243.08
[58] Field of Search .......... 422/68.1, 69.70, 422/82, 82.01, 82.02, 82.03, 108, 111; 436/43, 51, 55; 210/96.2, 143, 739; 423/243.08

[56] References Cited

U.S. PATENT DOCUMENTS

| | | | |
|---|---|---|---|
| 4,431,618 | 2/1984 | Boward, Jr. et al. | 423/242 |
| 4,582,692 | 4/1986 | Hamanaka et al. | |
| 4,677,077 | 6/1987 | Onizuka et al. | 436/50 |
| 4,683,211 | 7/1987 | Onizuka et al. | 436/50 |
| 4,687,649 | 8/1987 | Kuroda et al. | 423/242 |
| 4,994,246 | 2/1991 | Moser et al. | 423/242 |
| 5,168,065 | 12/1992 | Jankura et al. | 436/55 |
| 5,246,677 | 9/1993 | Moser et al. | 423/243.08 |
| 5,340,547 | 8/1994 | Moser et al. | 422/177 |
| 5,505,854 | 4/1996 | Glover et al. | 210/739 |

FOREIGN PATENT DOCUMENTS

| | | |
|---|---|---|
| 61-234913 | 10/1986 | Japan. |
| 2266117 | 11/1987 | Japan. |
| 3-127612 | 5/1991 | Japan. |

*Primary Examiner*—Nina Bhat
*Attorney, Agent, or Firm*—Sixbey, Friedman, Leedom & Ferguson, P.C.; Donald R. Studebaker

[57] ABSTRACT

An on-line control and monitoring system for automatically and continuously analyzing key process indicators in a wet lime/limestone flue gas desulfurization process is provided. The on-line control and monitoring system obtains a slurry and/or a slurry flitrate which is directed at selected fluid flow rates to one or more analytical devices each selected to analyze a flue gas desulfurization process indicator. Data is provided to a data acquisition system which processes the analysis results from the analytical devices and provides flue gas desulfurization process control information. This on-line monitoring and control system can be used to monitor and control the addition rate of performance enhancement additives such as organic acids, thiosulfate, oxidation air and the like.

10 Claims, 3 Drawing Sheets

FIG.2
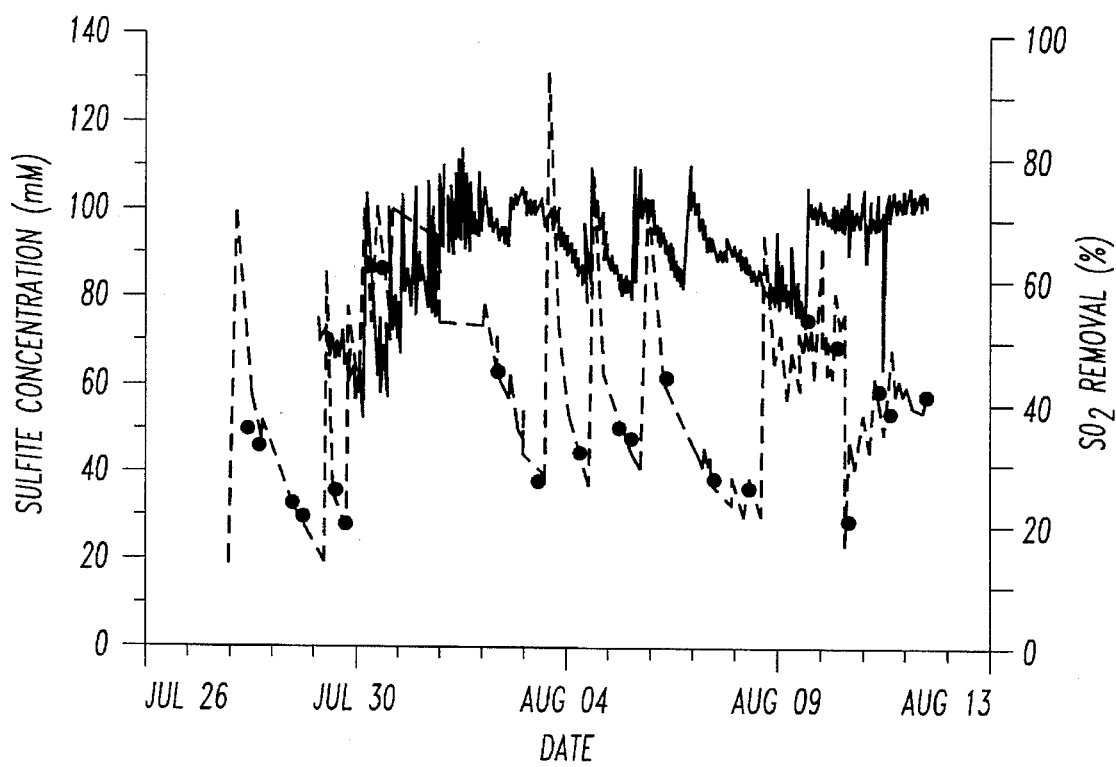
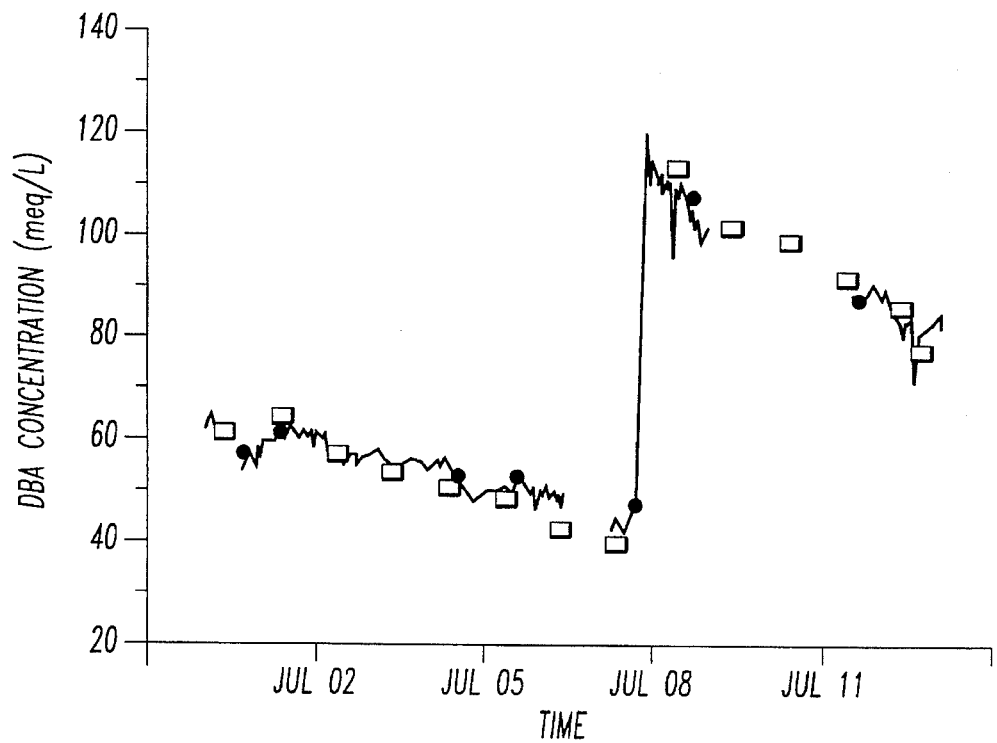
FIG.3

5,601,784

ON-LINE CONTROL AND MONITORING SYSTEM FOR WET LIME/LIMESTONE FLUE GAS DESULFURIZATION PROCESS

TECHNICAL FIELD

The present invention relates generally to flue gas desulfurization control and monitoring systems and specifically to an on-line control and monitoring system for automatically analyzing flue gas desulfurization process slurry to control and monitor the flue gas desulfurization process in response to on-line analytical measurement.

BACKGROUND OF THE INVENTION

Currently available flue gas desulfurization processes use a number of reagents and performance additives to scrub sulfur dioxide from the flue gas and to enhance or control scrubber operation. Reagents, such as limestone or lime, are added to the scrubber as a slurry to serve as a source of the alkalinity for scrubbing the sulfur dioxide. Organic acids may be added to the alkaline slurries to enhance scrubber performance in removing sulfur dioxide. Oxidation may be forced by the addition of oxidation air or inhibited by the addition of thiosulfate. Other additives may also be used to affect various aspects of the flue gas desulfurization process. With the exception of lime or limestone, the addition rates of most of these additives are usually not automatically controlled in response to a feedback control logic from an on-line analytical measurement. Lime or limestone addition rates are typically controlled in response to measurement of the pH of the process slurry. However, unless some type of control is exerted over reagent or additive addition, it is difficult to adjust reagent or additive usage to the level required to efficiently achieve the required sulfur dioxide removal or the desired benefit of the additive.

The objective in controlling additive or reagent addition is generally to minimize reagent usage while concurrently achieving the required sulfur dioxide removal or the maximum benefit of the additives. In the past, additive addition rates have typically been set at fixed rates which were determined from past plant operating experience. However, this practice has not met the control objective of maintaining the concentration of the flue gas desulfurization process additive at a level required to achieve the needed benefit of the additive. This approach provides no capability for adjusting the additive addition rate in response to changing process conditions or as needed to maximize the benefit of the additive while simultaneously minimizing usage and cost.

The prior art has suggested methods and systems for measuring various flue gas desulfurization system parameters and making the necessary adjustments to enhance sulfur dioxide removal. For example, U.S. Pat. No. 5,168,065 to Jankura et al. discloses the measurement of pH values as a basis for adjusting the amount of air supplied to a flue gas desulfurization reaction tank to maximize oxidation. Oxidation is measured indirectly by directly measuring the pH of the absorber circulating slurry. A feedback control adjusts the amount of air to the tank.

U.S. Pat. No. 4,677,077 to Onizuka et at. describes a method for continuously measuring the calcium carbonate concentration in a slurry such as an absorption liquid slurry used in a wet lime flue gas desulfurization process. This method may effectively measure the slurry calcium carbonate concentration. However, it is not suggested that the measurement method disclosed by Onizuka et al. could be used in conjunction with an on-line automatic monitoring and control system to adjust the conduct of a flue gas desulfurization process. Neither is it suggested that an automatic on-line monitoring and control system which monitors flue gas desulfurization process indicators in slurry flitrate could be integrated with such a slurry measurement system.

U.S. Pat. No. 4,582,692 to Hamanaka et al. discloses a flue gas desulfurization process wherein pH is automatically detected and regulated in connection with a number of pumps which are then set according to the amount of exhaust load in the absorber to control lime and limestone addition.

The control of the circulating flow rate of absorbing liquid slurry and slurry flow volume in flue gas desulfurization processes has also been disclosed by the prior art. Japanese Patent Publication Nos. 2266117 and 361234913 disclose controllers that accomplish this. Japanese Patent Publication No. 3127612 discloses an on-line desulfurization process performance indicator that detects the inlet sulfur dioxide concentration, the outlet sulfur dioxide concentration, pH and recirculating flow rate to control the circulating flow rate of absorbing liquid.

The prior art does not suggest the use of automatic on-line analyzers for monitoring and controlling the addition of flue gas desulfurization process performance enhancement additives or process control additives other than oxidation air and carbonate concentration. A need exists for an automatic on-line analysis system for analyzing filtered and unfiltered slurry in a flue gas desulfurization system to measure and control, as necessary, the addition rate of flue gas desulfurization process control or performance enhancement additives and to monitor key process control indicators.

SUMMARY OF THE INVENTION

It is a primary object of the present invention, therefore, to overcome the disadvantages of the prior art and to provide an on-line automatic analysis system for monitoring and controlling flue gas desulfurization system performance enhancement and process control additives.

It is another object of the present invention to provide an on-line system to analyze automatically a flue gas desulfurization process slurry to measure and control the addition rate of flue gas desulfurization process additives.

It is a further object of the present invention to provide an automatic on-line analysis system for a flue gas desulfurization process to monitor key process control indicators.

It is yet another object of the present invention to provide a flue gas desulfurization system including an automatic on-line analyzer system for analyzing the scrubbing liquor to achieve maximum benefits, reduce waste and minimize cost.

It is yet a further object of the present invention to provide an automatic on-line analyzer system which uses a combination of analyzers to monitor and control a flue gas desulfurization process.

The foregoing objects are achieved by providing an on-line control and monitoring system for a flue gas desulfurization system that employs a slurry to scrub undesirable sulfur dioxide from flue gas. The on-line control and monitoring system automatically analyzes a sample of filtrate from filtered scrubbing slurry that is directed to at least one analyzer. The analysis data relating to selected key process control indicators for the flue gas desulfurization process is transmitted to a data acquisition and processing system. This data is recorded and read to obtain the information desired, and the flue gas desulfurization process is modified as required according to the key process control indicators to conduct the flue gas desulfurization process as efficiently and effectively as possible. At least one analyzer that analyzes unfiltered flue gas desulfurization process slurry can also be included in the system.

Other objects and advantages will be apparent from the following description, claims and drawings.

BRIEF DESCRIPTION OF THE DRAWINGS

FIG. 2 presents graphically a comparison of on-line analysis according to the present invention, laboratory analysis and ion chromatography for sulfite concentration and $SO_2$ removal in a flue gas desulfurization process;

FIG. 3 presents graphically a comparison of on-line analysis according to the present invention and laboratory analysis of DBA (dibasic acid) concentration in a forced oxidation flue gas desulfurization process.

DESCRIPTION OF THE PREFERRED EMBODIMENTS

Most flue gas desulfurization processes require the use of some type of reagent to serve as a source of alkalinity to scrub sulfur dioxide from flue gas. The reagents most commonly used for this purpose in wet flue gas desulfurization systems are lime and limestone. The lime or limestone is normally added to the flue gas desulfurization process in the form of a slurry. Other reagents or additives may also be added to enhance scrubber performance or to control scrubber operation. Such additives include, for example, organic acids, thiosulfate and oxidation air. Of these reagents and additives, the only ones that are currently monitored and automatically controlled are lime and limestone and sometimes oxidation air. The lime or limestone addition rate can be controlled automatically in response to a feed-back control logic from an on-line analytical measurement. The addition rates of these reagents are presently controlled by obtaining a pH measurement of the process slurry. The control objective is to minimize reagent usage while at the same time maintaining sufficient alkalinity in the slurry to achieve the required level of sulfur dioxide removal.

Heretofore, the addition rates of reagents and additives other than lime or limestone have been set at fixed rates determined from plant operating experience. The control objective is to maintain the concentration of the additive or reagent at a level required to achieve the required benefit of the additive or reagent. However, this fixed rate approach provides no capability for adjusting the additive or reagent addition rate in response to changing flue gas desulfurization process conditions or as needed to maximize the benefit of the additive or reagent while concurrently minimizing usage and cost.

The present invention resides in an automatic on-line analysis system for a flue gas desulfurization process which automatically monitors and controls the addition rate of flue gas desulfurization performance enhancement or process control additives and monitors key process control indicators. This on-line analysis system may include such automatic analysis devices as automatic titrators, automatic colorimeters, conductivity monitors, automatic ion chromatographs, ion specific electrodes and/or available automatic analysis devices useful for monitoring desired flue gas desulfurization process parameters. One or more analyzers may be used to monitor the flue gas desulfurization process.

Figure 1:
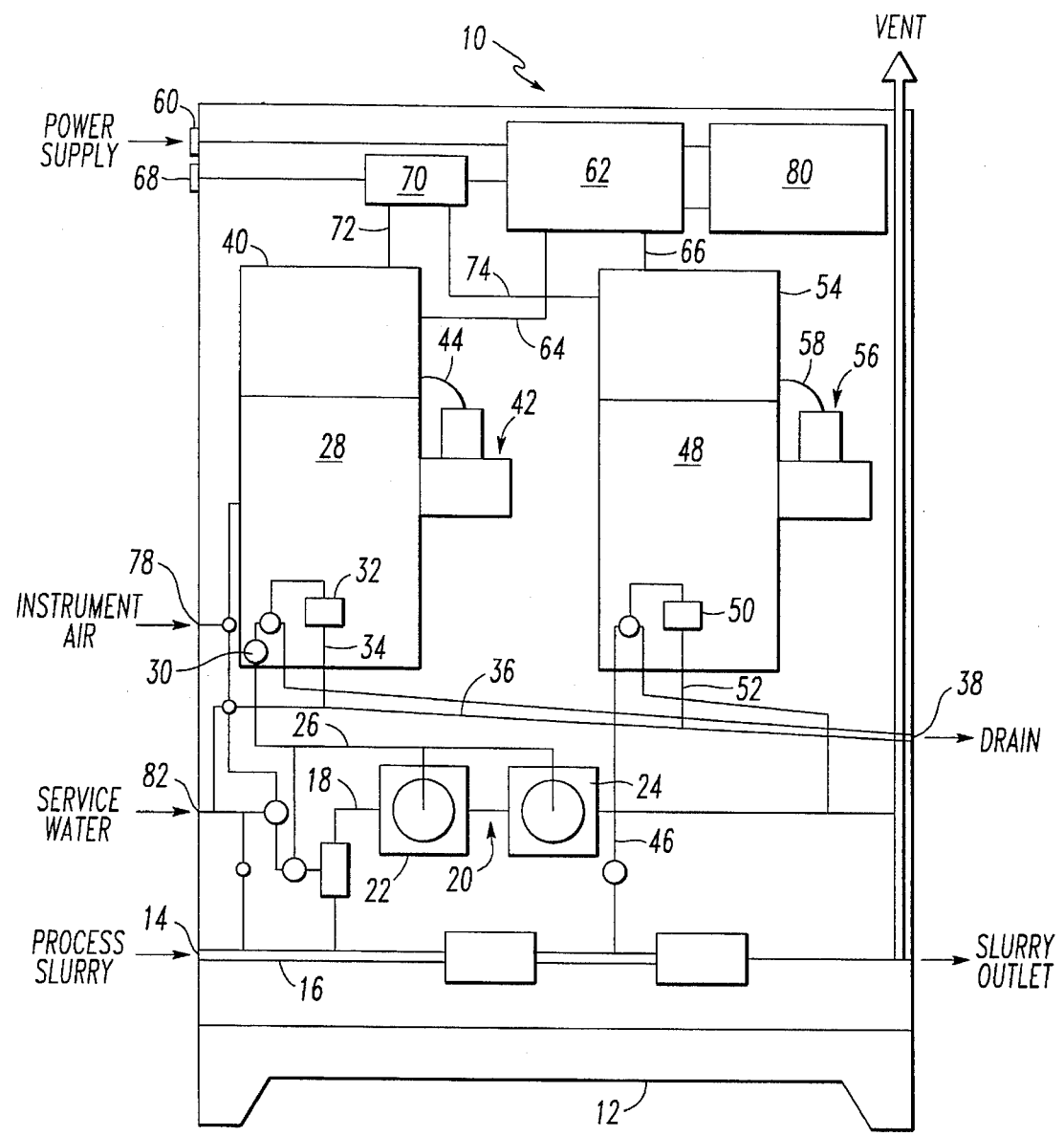
FIG. 1 illustrates schematically one embodiment of an on-line flue gas desulfurization control and monitoring system in accordance with the present invention.

FIG. 1 illustrates an example of one embodiment of an automatic on-line analysis and monitoring system for a flue gas desulfurization process. The analysis system shown in the drawing is used to perform frequent analyses of the flue gas desulfurization scrubbing slurry or filtered liquor to determine the concentration of a selected additive or the value of a process control indicator affected by the additive. The concentration measurement may then be used to adjust the feed rate of the additive in response to changing flue gas desulfurization conditions or to process upsets.

Referring to FIG. 1, the on-line control and monitoring system 10 of the present invention is shown contained within a housing 12 which supports the analyzers, the required fluid connections, the control system and a continuous filtration system. The continuous filtration system which filters the flue gas desulfurization process slurry to provide an uninterrupted supply of slurry flitrate that will not clog the analyzers, is described in commonly owned copending U.S. patent application Ser. No. 08/302,432, filed Sep. 9, 1994, now U.S. Pat. No. 5,505,854, entitled CONTINUOUS FILTRATION SYSTEM, the disclosure of which is hereby incorporated herein by reference. Slurry is obtained from a wet flue gas desulfurization process such as one of the flue gas desulfurization processes described in commonly owned U.S. Pat. Nos. 4,994,246, issued Feb. 19, 1991, and 5,340,547, issued Aug. 23, 1994, the disclosures of which are hereby incorporated herein by reference. The slurry is directed into the on-line control and monitoring system 10 through a process slurry inlet 14. The slurry is then directed through a slurry inlet line 16 and a filter system line 18 to a filter system 20. The slurry is directed through a pair of filters 22 and 24 connected in series in the filter system 20 where it is filtered to produce a solids-free filtrate. The flitrate is directed along a filtrate line 26 from the filter system 20 to an analyzer 28. The filtrate enters the analyzer 28 through a valve 30 to an analyzer cell 32, where the analytical process is actually conducted. Following the analysis, the spent filtrate leaves the analyzer 28 through an outlet line 34 to a drain line 36, which is connected to a gravity drain 38.

The analyzer 28 includes a section 40 which contains the electronics and electrical connections required to perform the analysis and to generate and transmit data from the analytical process. A reagent storage module 42, which is connected to the analyzer reagent pump (not shown) and cell 32 by a connection 44, meters reagents and solutions to the analyzer cell as required to conduct the analysis.

It is often desirable to conduct analysis on unfiltered flue gas desulfurization process slurry to monitor carbonate loading or other slurry solids indicators. Therefore, the analysis system of the present invention provides an analyzer for this purpose. Process slurry is directed to the analyzer 48 from the slurry inlet line 16 through a slurry supply line 46. The unfiltered slurry is analyzed in an analyzer cell 50 and then leaves the analyzer 48 through an outlet 52 and flows into the drain line 36. The analyzer 48 also includes a section 54 which contains the electronics and electrical connections and a reagent storage module 56, which is connected to the analyzer reagent pump (not shown) and cell 50 by a connection 58, to meter the addition of reagent and solutions.

A power supply 60, which is preferably 110 volts of alternating current, provides power to the analyzers 28 and 48 through a circuit box 62 and electrical connections 64 and 66, respectively. An auxiliary power supply may also be provided.

A data acquisition system input/output link 68 is provided with appropriate connections to a data link 70 and to each analyzer 28 and 48 through respective connectors 72 and 74. Signals, from analyzers 28 and 48 which correspond to analysis data may be in analog (4–20 mA) or digital (RS 232) form. A suitable connector can be connected to the data acquisition system so that the data generated by the analyzers can be transmitted to a computer, which may be a personal computer. The data may be recorded or read instantaneously. Feedback loops can be connected to the data acquisition system input/output link so that the analysis results can be used to control selected parameters of the flue gas desulfurization process. The real time results from the analysis of the flue gas desulfurization process slurry indicators can be used as the basis for altering or changing the process as it is being conducted.

The on-line control and monitoring system embodiment shown in FIG. 1 also provides a source of instrument air 78 to keep the analyzer electronics vented and cool and to actuate valves. An automatic filter flushing mechanism is also provided to keep the filters 22 and 24 free from solids and capable of providing a consistent supply of slurry filtrate to analyzer 28 and other analyzers which may be incorporated into the system that require slurry filtrate for analysis. An autoflush control 80 automatically activates the filter flushing mechanism in response to a predetermined signal, which could be, for example, a selected number of analyses or a time interval. Activation of the filter flushing mechanism causes the filter system to be isolated from the process slurry inlet line 16 and the analyzer 28 by selectively actuating valves in the fluid lines. A supply of water from a service water inlet 82 is routed under pressure from the filtrate side to the slurry side of the filter system 20 to clean solid particles from the filter media (not shown). The automatic flushing system operates for a predetermined period of time and is then deactivated so the analysis system can operate again.

The configuration of analyzers shown in FIG. 1 is merely exemplary of one possible arrangement. For example, the analyzer 28 could be a photometric autotitrator, and the analyzer 48 could be a potentiometric autotitrator. Additional analyzers could be included in the system, and all of the analyzers could be set up to analyze slurry flitrate instead of a combination of slurry flitrate and unfiltered slurry. The analyzers chosen for use in the control and monitoring system of the present invention will depend on the specific flue gas desulfurization process control indicators or performance enhancement additives to be analyzed or monitored by the control and monitoring system. Analytical devices such as conductivity meters, automatic titrators, automatic colorimeters, automatic ion chromatographs and ion specific electrodes can be included in the present on-line monitoring system. The number of such analytical devices will depend on the number of key flue gas desulfurization process control indicators or parameters to be monitored.

The flow rate of the slurry flitrate through the control and monitoring system of the present invention may be regulated as required to provide a desirable flow of flitrate to the components of the system at a flow rate appropriate for the particular analytical device. For example, a conductivity meter may require a fluid flow on the order of 10 milliliters per minute, while an automatic titrator requires a fluid flow of about 50 milliliters per minute.

One example which illustrates the use of on-line analyzers to control the addition of flue gas desulfurization performance enhancement or process control additives is the measurement of the liquid phase alkalinity to control the rate of organic acid additives. Organic acid additives are used to increase sulfur dioxide removal efficiency by increasing the scrubbing capacity of the scrubbing liquor. The on-line monitoring measurement is used to control the organic acid concentration to maintain an optimum level of liquid phase alkalinity to achieve the desired sulfur dioxide removal efficiency. Control of the organic acid addition minimizes waste while maintaining required removal efficiencies during process upset conditions.

On-line analyzers may also be used to monitor the gypsum relative saturation or measure the thiosulfate concentration so that the thiosulfate addition rate can be controlled. Thiosulfate is used to inhibit the oxidation of absorbed sulfur dioxide or the oxidation of sulfite to sulfate. Experience has shown that if the rate of oxidation of a flue gas desulfurization process can be sufficiently inhibited, the process liquor will be subsaturated with respect to gypsum. The value of the gypsum relative saturation will therefore be less than one. Operation of the flue gas desulfurization process at a gypsum saturation of less than one minimizes the potential for gypsum scaling to occur. In addition, controlling the flue gas desulfurization process with thiosulfate at very low levels of sulfite oxidation and gypsum saturation will produce very pure calcium sulfite solids. Such solids exhibit improved handling, filtering and dewatering properties as compared to conventional calcium sulfite-sulfate solid solution solids.

The flue gas desulfurization control and monitoring system of the present invention can additionally be used to measure dissolved sulfite in the slurry flitrate to control the air sparging rate in a forced oxidation process. This control scheme, in addition to allowing air compressors to operate in a most efficient manner, insures that sulfite levels do not build up to a point where inhibited dissolution of limestone or sulfite blinding occurs.

Figure 4:
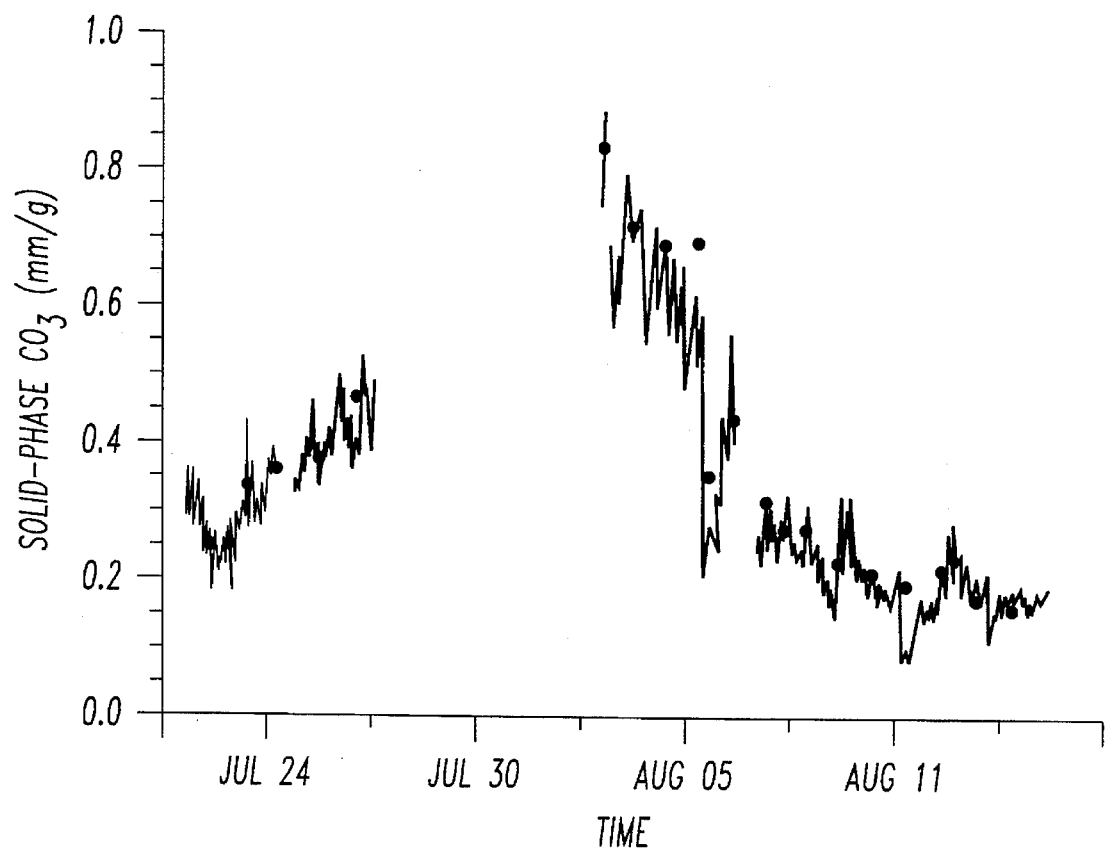
FIG. 4 presents graphically a comparison of on-line analysis according to the present invention and laboratory analysis for solid phase carbonate to determine limestone loading in a forced oxidation flue gas desulfurization process.

FIGS. 2, 3 and 4 present, graphically, comparisons between data obtained by the on-line analysis of various flue gas desulfurization process control indicators and the conventional laboratory analysis of these indicators. Sulfite concentrations obtained over an 18 day period are presented with $SO_2$ removal data during the same period in FIG. 2. These data were collected during a magnesium-enhanced, lime reagent flue gas desulfurization process test series. The spikes that can be observed in the on-line sulfite concentration data are due to the addition of the magnesium-lime reagent. This conclusion is supported by the coincidental spikes that can be observed in the $SO_2$ removal data and indicates the sensitivity of the on-line sulfate monitor to changing process conditions. Good agreement can also be observed between the on-line and laboratory sulfite data suggesting that, in addition to being sensitive to changing conditions, the on-line data is also very reliable.

FIG. 3 is a historical trend-plot showing the DBA (dibasic acid) concentration during a forced oxidation flue gas desulfurization process test series. The solid line in FIG. 3 shows the on-line analyzer DBA measurements, while the solid circles and open squares show the corresponding DBA concentration measured in the laboratory by buffer capacity (BC) titration and the DBA concentration measured by ion chromatography (ICE). The agreement of the on-line measurements and the laboratory measurements attests to the capability of the on-line monitoring system to accurately measure DBA concentration under these operating conditions.

The analyses presented in FIGS. 2 and 3 were conducted on flue gas desulfurization process slurry flitrate, while the analysis presented in FIG. 4 was conducted on unfiltered flue gas desulfurization process slurry by a potentiometric analyzer such as analyzer 48 in FIG. 1.

FIG. 4 shows historical solid-phase carbonate data during a forced oxidation flue gas desulfurization process test series to determine limestone loading. Good agreement between the on-line analyzer data and laboratory is clearly evident, attesting to the reliability of the on-line measurement of this parameter under these operating conditions.

Results of the evaluation of on-line methods to measure soluble calcium and soluble total hardness concentrations are presented in Tables I and II below. Shown in these tables are the $Ca^{++}$ and $Mg^{++}$ concentrations of the various synthetic solutions which were tested, and a summary of test results for each test solution showing the average concentration measured, the percent coefficient of variation, the 95% standard error confidence interval, the number of measurements that were made, and the percent deviation from the known or true concentration of the test solution. The test results showed that both the calcium and total hardness on-line monitoring procedures are capable of achieving a high level of precision. This is indicated by the low coefficient of variation values which ranged from 0.74% to 3.4% for calcium and 0.24% to 1.28% for total hardness. The accuracy of the on-line monitor procedures, as indicated by the % deviation from the true concentration value, was also acceptable ranging from −0.9% to 6.4% for calcium and −2.0% to 8.3% for total hardness.

Another example of the use of the control and monitoring process of the present invention would be the measurement of dissolved sulfite to control the air sparging rate in a forced oxidation flue gas desulfurization process. Monitoring the sulfite concentration would allow the air compressors to operate efficiently and would insure that sulfite levels did not build up to a point at which the dissolution of limestone was inhibited and sulfite blinding occurred. Other process indicators such as chloride concentration and sulfate concentration can also be monitored with the system of the present invention. The chloride concentration can be an especially important indicator in a forced oxidation flue gas desulfurization system which produces wallboard quality gypsum. A low chloride concentration in the gypsum solids is required to meet the manufacturing specifications for gypsum wallboard. The sulfate concentration in conjunction with the previous calcium concentration measurement could be used as an indicator of gypsum relative saturation.

A combination of analyzers may be used in the control and monitoring system of the present invention to monitor and control the feed rates of a combination of different additives to a flue gas desulfurization process. Further, data obtained from one analyzer can be used to verify the reliability of data obtained from other analyzers. Moreover, the use of on-line analyzers in a flue gas desulfurization system in conjunction with performance enhancement additives allows the maximum benefit of the additives to be achieved and consistently maintained. The present invention should minimize additive waste and, as a result, minimize the cost associated with the use of flue gas desulfurization process additives.

INDUSTRIAL APPLICABILITY

The on-line flue gas desulfurization process control and monitoring system of the present invention will find its primary applicability where it is desired to carefully monitor

TABLE I

| Test Solution | | Average Measured Ca | Coefficient of Variation | Standard | Number of | % Deviation from |
|---|---|---|---|---|---|---|
| Ca (mM) | Mg, (mM) | (mM) | (%)* | Error** | Measurements | True Value |
| 20 | 66 | 20.4 | 0.74 | 0.03 | 92 | 1.9 |
| 31 | 16 | 31.7 | 1.55 | 0.13 | 55 | 2.3 |
| 10 | 16 | 10.6 | 0.85 | 0.02 | 57 | 6.4 |
| 10 | 33 | 10.1 | 3.47 | 0.11 | 38 | 1.3 |
| 10 | 66 | 9.91 | 2.52 | 0.04 | 120 | −0.9 |

*Coefficient of Variation (%) = (Standard Deviation/Mean) × 100
**95% Confidence Interval

TABLE II

| Test Solution | | | Average Measured Hardness (mM) | Coefficient of Variation (%)* | Standard Error** | Number of Measurements | % Deviation from True Value |
|---|---|---|---|---|---|---|---|
| Ca, (mM) | Mg, (mM) | Total Hardness, (mM) | | | | | |
| 10 | 33 | 43 | 43.4 | 1.01 | 0.05 | 331 | 0.9 |
| 20 | 66 | 86 | 84.3 | 0.24 | 0.06 | 39 | −2.0 |
| 20 | 16 | 36 | 39.0 | 1.28 | 0.62 | 5 | 8.3 |

*Coefficient of Variation (%) = (Standard Deviation/Mean) × 100
**95% Confidence Interval and control key flue gas desulfurization process indicators to maximize the efficiency and minimize waste in the conduct of the flue gas desulfurization process.

We claim:

1. An on-line control and monitoring system for monitoring selected process control indicators and parameters in a wet lime/limestone flue gas desulfurization process for removing sulfur dioxide from flue gas, wherein said control and monitoring system operates concurrently with the conduct of the flue gas desulfurization process to provide data relative to selected process control indicators and parameters that can be used to control the conduct of the flue gas desulfurization process while the flue gas desulfurization process is operating, wherein said on-line control and monitoring system comprises:

(a) a housing supporting said on-line control and monitoring system;

(b) a supply of flue gas desulfurization process slurry withdrawn from said flue gas desulfurization process while said flue gas desulfurization process is being conducted and directed through a fluid conducting conduit to a continuous filtration system mounted in said housing;

(c) said continuous filtration system being fluidically connected to at least one automatic analyzer mounted in said housing to filter said process slurry supply to provide a continuous supply of analytical quality slurry filtrate;

(d) said at least one automatic analyzer being capable of automatically quantitatively analyzing said slurry filtrate at selected intervals to produce data relating to a selected flue gas desulfurization process control indicator or parameter; and (e) a control system operationally connected to said automatic analyzer and to said flue gas desulfurization process capable of receiving and processing the data produced by said analyzer and making any adjustments in the conduct of the flue gas desulfurization process indicated by said data to be necessary to optimize sulfur dioxide removal efficiency.

2. The on-line control and monitoring system described in claim 1, wherein said selected process control indicators and parameters include gypsum relative saturation, sulfite concentration, magnesium concentration, chloride concentration, calcium concentration, sulfate concentration, sulfur dioxide removal and total carbonate.

3. The on-line control and monitoring system described in claim 1, wherein the analyzer is selected from the group consisting of automatic titrators, automatic colorimeters, conductivity monitors, automatic ion chromatographs and ion specific electrodes.

4. The on-line control and monitoring system described in claim 1 wherein said analyzer is operatively connected to said control system to be activated to conduct a selected analysis at a selected interval.

5. The on-line control and monitoring system described in claim 1, wherein said system further includes an analyzer fluidically connected directly to said slurry supply and electronically connected to said control system, and said analyzer is capable of automatically quantitatively analyzing said slurry to produce data relating to process indicators of said slurry and transmitting said data to said control system.

6. The on-line control and monitoring system described in claim 5, wherein said analyzer is a potentiometric autotitrator.

7. The on-line control and monitoring system described in claim 6, wherein said analyzer quantitatively measures solid phase carbonate and said control system adjusts limestone addition to said flue gas desulfurization process.

8. The on-line control and monitoring system described in claim 5, wherein said control system includes a data link operatively connected to each said analyzer and to a data acquisition system capable of recording and reading data generated by said analyzers.

9. The on-line control and monitoring system described in claim 8, wherein said control system further includes a feedback loop operatively connected to said flue gas desulfurization process to control the addition of at least one flue gas desulfurization process additive in response to the data from said analyzer relating to a process control indicator affected by said additive.

10. An on-line control and monitoring system for monitoring selected process control indicators and parameters in a wet lime/limestone flue gas desulfurization process for removing sulfur dioxide from flue gas, wherein said control and monitoring system operates concurrently with the conduct of the flue gas desulfurization process to provide data relative to the selected process control indicators and parameters that can be used to control the conduct of the flue gas desulfurization process while said flue gas desulfurization process is operating, wherein said on-line control and monitoring system comprises:

(a) a housing supporting said on-line control and monitoring system;

(b) a supply of flue gas desulfurization process slurry withdrawn from said flue gas desulfurization process while said flue gas desulfurization process is being conducted and directed through a fluid conducting conduit to a continuous filtration system mounted in said housing;

(c) said continuous filtration system being fluidically connected to at least one automatic analyzer mounted in said housing to filter said process slurry supply to provide a continuous supply of analytical quality slurry filtrate;

(d) said at least one automatic analyzer capable of automatically quantitatively analyzing said slurry filtrate at selected intervals to produce data relating to said selected flue gas desulfurization process control indicator or parameter;

(e) a control system operationally connected to said automatic analyzer and to said flue gas desulfurization process capable of receiving and processing the data produced by said analyzer and making any adjustments in the conduct of the flue gas desulfurization process indicated by said data to be necessary to optimize sulfur dioxide removal efficiency; and (f) at least one automatic analyzer mounted in said housing fluidically connected directly to said slurry supply and electronically connected to said control system capable of automatically quantitatively analyzing said slurry to produce data relating to process indicators of said slurry and transmitting said data to said control system.

* * * * *